United States Patent [19]

Meno

[11] Patent Number: 4,546,779

[45] Date of Patent: Oct. 15, 1985

[54] METHOD OF MEASUREMENT OF EUSTACHIAN TUBE OPENING AND ASSOCIATED APPARATUS

[75] Inventor: Frank Meno, Pittsburgh, Pa.

[73] Assignee: University of Pittsburgh, Pittsburgh, Pa.

[21] Appl. No.: 560,143

[22] Filed: Dec. 12, 1983

[51] Int. Cl.⁴ .............................................. A61B 5/12
[52] U.S. Cl. .................................................. 128/746
[58] Field of Search ............... 128/746, 739, 773, 774

[56] References Cited

U.S. PATENT DOCUMENTS 4,429,702  2/1984  Von Recklinghausen ......... 128/746

FOREIGN PATENT DOCUMENTS 2459648  1/1981  France .
0760955  9/1980  U.S.S.R. ............................. 128/746

OTHER PUBLICATIONS

Cabot, et al., "Detection of Phase Shifts in Harmonically Related Tones", *Journ. of Audio Engr. Soc.*, vol. 24, No. 7, 9-1976, pp. 568-571.

Primary Examiner—Lee S. Cohen
Assistant Examiner—Angela D. Sykes
Attorney, Agent, or Firm—Arnold B. Silverman

[57] ABSTRACT

A sound wave signal is applied to the nasal cavity and is picked up at the auditory canal of the ear of a subject. The phase difference between the two signals is a measure of the extent of opening of the Eustachian tube. By converting the two sound signals to electrical signals and transmitting them to a phase comparator it is possible to ascertain the changes in opening of the Eustachian tube during swallowing.

11 Claims, 1 Drawing Figure

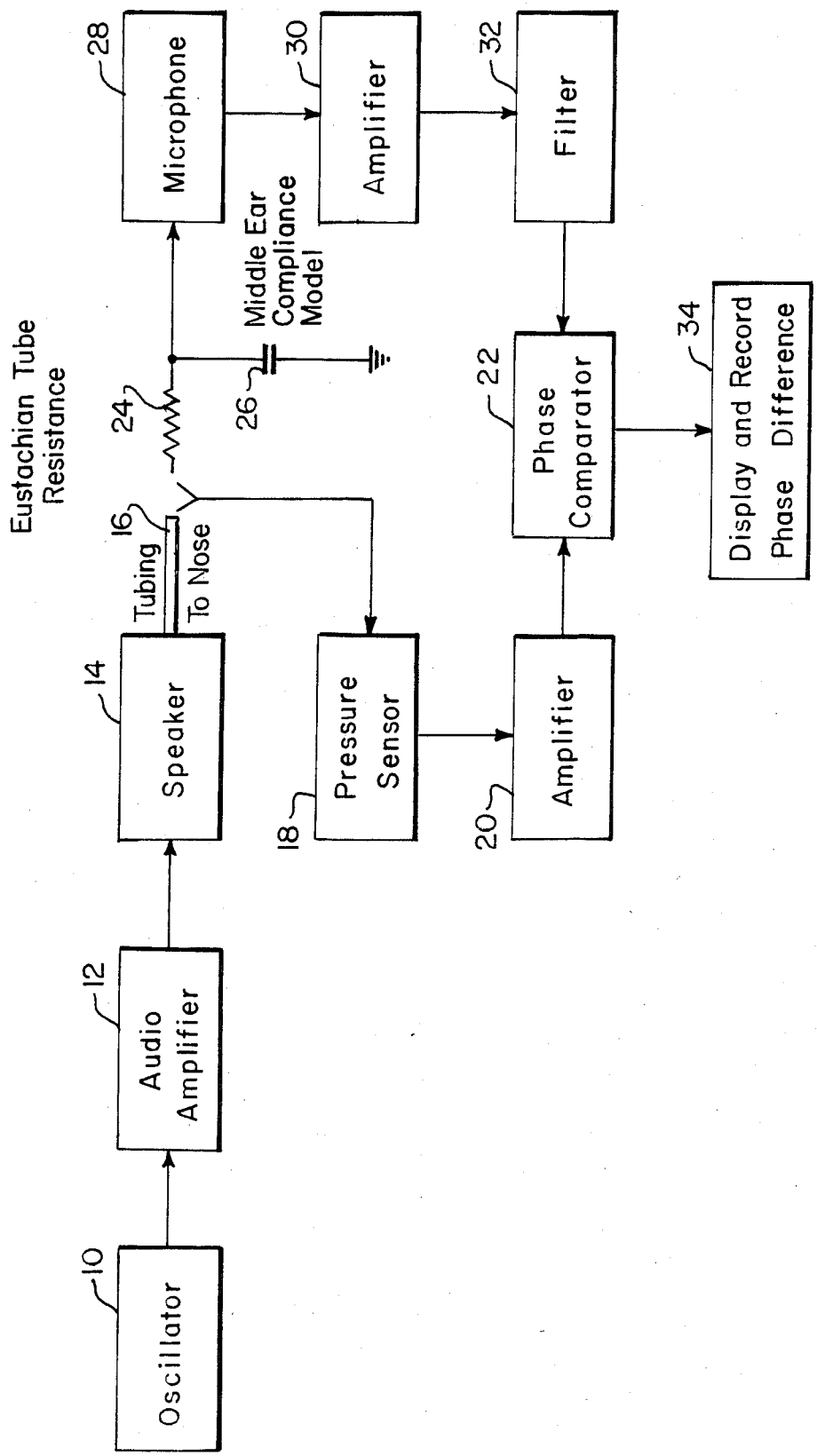

METHOD OF MEASUREMENT OF EUSTACHIAN TUBE OPENING AND ASSOCIATED APPARATUS

BACKGROUND OF THE INVENTION

1. Field of the Invention

This invention relates to a method and apparatus to determine the extent and changes in the extent with time of Eustachian tube opening of a subject by measuring the phase difference and changes in the phase difference with time of sound waves applied to the nose and detected in the ear canal of a subject.

2. Description of the Prior Art

French Pat. No. 2,459,648 teaches a method for measuring Eustachian tube opening wherein a signal of determined frequency is applied at the nostril of a subject, is transmitted through the Eustachian tube during swallowing and, finally, is picked-up and measured in the ear. The patent states that the peak amplitude of the signal picked up in the ear indicates the diameter of the opening of the Eustachian tube. However, the patent further states that the signal picked up by the auricular probe is likely to be fugitive and subject to interference. Therefore, the patented method prohibits measurement of the amplitude if the signal picked up does not show a predetermined number of consecutive impulses, i.e. does not last for a predetermined time.

As the method of the French patent publication measurement of fleeting or fugitive amplitudes, it is substantially incapable of measuring rapidly changing opening sizes such as occur when the Eustachian tube diameter is changing rapidly from its fully closed state upon the onset of swallowing or from its fully open state at the end of a swallow.

There remains a need, for both clinical and research purposes, to obtain information concerning changes in the amount of Eustachian tube opening as a function of time, which involves determinations concerning the tube while its diameter is changing from its fully closed to open state and vice versa.

SUMMARY OF THE INVENTION

The present invention utilizes phase sonometry. It provides a method and apparatus to determine the amount of Eustachian tube opening and changes in the opening as a function of time by measuring the difference of phase at a given time between the sound wave in the nose and in the auditory canal of the subject under test. The French patent does not relate in any way to measurement of sound wave phase differential between the nose and the auditory canal. By employing a phase differential method, the present invention avoids the many difficulties involving random resonances in the body that can cause the fugitive and interference signals mentioned in the French patent. In addition, the French patent teaches the use of a fixed, determined frequency in order to measure the duration of any particular opening by counting consecutive impulses. In contrast to the method of the French patent, the present invention is not limited to any particular frequency, but a frequency sweep can be implemented to determine an optimum frequency for each patient tested. Finally, the opening of the Eustachian tube is changing most rapidly at the beginning and end of a swallow. These are the times the differential measured by the present method is the largest and easiest to measure but these measurements are most apt to be prohibited according to the French patent because they are the most transitory.

In summation, the present invention measures the phase shift between electrical signals in the nose and in the ear representing the phase shift in sound signals at the same locations in order to alleviate the problems inherent in the amplitude measurement method of the French patent, due to various resonances in the passageways of the nose and the ear.

The Eustachian tube represents a variable resistance to air flow, depending upon the degree of opening during swallowing, from its normally closed condition. As the Eustachian tube extends from the nasal cavity to the middle ear, there is a pressure rise and fall in the middle ear depending upon the opening of the tube. As the middle ear represents a compliant chamber, its pressure will lag pressure changes in the nasal cavity. Consequently, by continuously measuring the phase delay, it will be possible to determine the amount of Eustachian tube opening as a function of time.

The present invention applies a sound wave signal obtained through an oscillator, audio amplifier and speaker to the nasal cavity where the applied signal induces sinusoidal air pressure waves. These pressure waves are detected by a pressure sensor or microphone in or adjacent the nasal opening, amplified and fed as a first electrical input signal to a phase comparator. A microphone is placed in or adjacent the ear to pick up the transmitted sound signal reaching the auditory canal and the signal detected in the ear is amplified, filtered and fed as a second electrical input impulse to a phase comparator. The output signal from the phase comparator, based on the input signal fed thereto, represents the phase shift or differential between the input and output sound signals and is both displayed and recorded versus time.

It is an object of the invention to provide a method and apparatus for measuring the opening and changes in the opening of the Eustachian tube as a function of time.

It is another object of the present invention to provide such a method and apparatus which may be employed efficiently without requiring extensive training of personnel or expensive equipment.

It is another object of the invention to provide such a method and associated apparatus which are adapted to provide rapid and accurate measurements.

These and other objects of the invention will be fully understood from the following description of the invention on reference to the illustrations appended hereto.

BRIEF DESCRIPTION OF THE DRAWING

The FIGURE presents a schematic diagram of a combination of elements arranged to measure the phase shift of sound waves between the nose and the ear. The individual elements in the combination are not described in detail because each is readily known to those skilled in the art.

DESCRIPTION OF THE PREFERRED EMBODIMENT

Referring to the FIGURE, an electrical signal of desired frequency is induced in oscillator 10 and is passed through audio amplifier 12 and speaker 14. The resulting sound signal leaving speaker 14 passes through tube 16 to the nose of an individual, such as a human patient, for example. The sound signal induces pressure waves in the nasal cavity of the patient which are detected by pressure sensor 18, amplified in amplifier 20 and transmitted as an input electrical signal to phase comparator 22.

The sound input to the nasal cavity passes through the Eustachian tube, which is symbolically represented as an electrical resistor 24 because it is subject to variable closure and opening, thus presenting a variable resistance to the passage through the inner ear which is a chamber and which is symbolically represented as a capacitor 26.

Sound waves passing through the inner ear enter the auditory canal where they are picked up by microphone 28 and converted to an electrical signal which is amplified in amplifier 30 and filtered to remove extraneous signals in filter 32. The output from filter 32 constitutes an electrical signal to phase comparator 22.

Phase comparator 22 produces an output signal which represents the phase shift between the input sound signal to the nasal cavity and the output sound signal picked up in the auditory canal and which can be displayed, computed and/or recorded by means 34. The extent of the phase shift will depend upon the relative opening of the Eustachian tube and can be correlated therewith, the shift being greater upon closure of the Eustachian tube and lesser upon opening of the Eustachian tube.

Whereas particular embodiments of the invention have been described above for purposes of illustration it would be evident to those skilled in the art that numerous variations of the details may be made without departing from the invention as defined in the appended claims.

I claim:

1. A method for determining the opening or changes in the opening with time of the Eustachian tube of a subject comprising applying an input sound wave signal to the nasal cavity of the subject, converting the input sound wave signal to a first electrical input signal, feeding said first electrical input signal to a phase comparator, picking up a related output sound wave signal at the ear of the subject, converting said output sound wave signal to a second electrical input signal, feeding said second electrical input signal to said phase comparator, and said phase comparator indicating the phase differential between said input sound wave signal and said output sound wave signal, whereby said phase differential may be employed to determine the opening or change in opening with time of said Eustachian tube.

2. The method of claim 1 including establishing sinusoidal pressure waves by means of said input sound wave signal, and sensing said sinusoidal pressure waves and converting them to said first electrical input signal.

3. The method of claim 2 wherein said input sound wave signal is provided by an oscillator, audio amplifier and speaker combination.

4. The method of claim 1 wherein said output sound wave signal is received by a microphone, amplifier and filter combination.

5. The method of claim 1 wherein said phase comparator displays said phase differential and records said phase differential versus time.

6. A sonometric apparatus for measuring Eustachian tube opening comprising oscillating sound producing means for providing a sound wave input signal to the nasal cavity of a subject; sound wave pick-up means for detecting said sound wave signal at the ear of the subject; first amplifier means for amplifying said sound wave input signal as a first electrical signal; second amplifier means for amplifying said sound wave signal picked-up at the ear as a second electrical signal; and phase comparator means for receiving and comparing said first electrical signal and said second electrical signal and emitting a signal corresponding to the phase difference between said first and second electrical signals, said phase difference being employed to to determine the opening or change in opening with time of said Eustachian tube.

7. The apparatus of claim 6 wherein said oscillating sound producing means includes oscillator means for creating a sound wave signal, audio amplifier means for amplifying said sound wave signal, and speaker means for emitting said sound wave signal, in combination.

8. The apparatus of claim 6 wherein said sound wave pick-up means includes microphone means for picking up said sound wave.

9. The apparatus of claim 6 wherein said first amplifier means includes pressure sensor-amplifier means in combination for sensing and amplifying sinusoidal pressure waves of the subject.

10. The apparatus of claim 6 wherein said second amplifier means comprises amplifier-filter means in combination for amplifying and filtering said sound wave signal picked up as a second electrical signal.

11. The apparatus of claim 6 including phase comparator display and recording means, and said phase comparator display and recording means being operatively associated with said phase comparator means to receive signals therefrom.

* * * * *

UNITED STATES PATENT AND TRADEMARK OFFICE
CERTIFICATE OF CORRECTION

PATENT NO. : 4,546,779

DATED : Oct. 15, 1985

INVENTOR(S) : Frank Meno

It is certified that error appears in the above-identified patent and that said Letters Patent is hereby corrected as shown below:

Column 1, line 19, "picked-up" should be --picked up--.

Column 1, line 29, "publication" should be --prohibits--.

Claim 6, column 4, line 20, "picked-up" should be --picked up--.

Claim 6, column 4, line 25, "employed to to" should be --employed to--.

Signed and Sealed this

Twentieth Day of May 1986

[SEAL]

Attest:

Attesting Officer

DONALD J. QUIGG

Commissioner of Patents and Trademarks